US010035041B2

(12) United States Patent
Jung

(10) Patent No.: US 10,035,041 B2
(45) Date of Patent: Jul. 31, 2018

(54) EXERCISE EVALUATION SYSTEM AND METHOD

(71) Applicant: FIT.LIFE INC., Gyeonggi-do (KR)

(72) Inventor: Yoo Suk Jung, Gyeonggi-do (KR)

(73) Assignee: FIT.LIFE INC., Gyeonggi-do (KR)

( * ) Notice: Subject to any disclaimer, the term of this patent is extended or adjusted under 35 U.S.C. 154(b) by 150 days.

(21) Appl. No.: 14/442,660

(22) PCT Filed: Sep. 16, 2013

(86) PCT No.: PCT/KR2013/008353
§ 371 (c)(1),
(2) Date: May 13, 2015

(87) PCT Pub. No.: WO2014/092306
PCT Pub. Date: Jun. 19, 2014

(65) Prior Publication Data
US 2016/0256742 A1    Sep. 8, 2016

(30) Foreign Application Priority Data

Dec. 13, 2012    (KR) .......................... 10-2012-0145298

(51) Int. Cl.
| | |
|---|---|
| A63B 24/00 | (2006.01) |
| G06Q 30/02 | (2012.01) |
| G09B 7/00 | (2006.01) |
| A61B 5/024 | (2006.01) |
| G09B 19/00 | (2006.01) |
| A61B 5/083 | (2006.01) |

(52) U.S. Cl.
CPC .......... *A63B 24/0062* (2013.01); *A61B 5/024* (2013.01); *A61B 5/0833* (2013.01); *A63B 24/0075* (2013.01); *G06Q 30/0201* (2013.01); *G09B 7/00* (2013.01); *G09B 19/003* (2013.01)

(58) Field of Classification Search
CPC ......................... G09B 19/003; A63B 24/0062
USPC ........................................................ 434/247
See application file for complete search history.

(56) References Cited

U.S. PATENT DOCUMENTS

| | | | | |
|---|---|---|---|---|
| 2008/0096726 | A1* | 4/2008 | Riley ................ | A63B 24/0006 482/8 |
| 2009/0069156 | A1* | 3/2009 | Kurunmaki ........ | A63B 24/0062 482/9 |

FOREIGN PATENT DOCUMENTS

| | | | | |
|---|---|---|---|---|
| KR | 10-2000-0054566 | 9/2000 | ............. | G06F 19/00 |
| KR | 10-2004-0025200 | 3/2004 | ............. | G06F 19/00 |
| KR | 10-2004-0106648 | 12/2004 | ............. | G06F 17/60 |
| KR | 10-2009-0002175 | 1/2009 | ............. | G06Q 50/00 |

(Continued)

OTHER PUBLICATIONS

International Search Report (ISR) dated Dec. 5, 2013 in PCT/KR2013/008353 with English translation.

*Primary Examiner* — Thomas Hong
(74) *Attorney, Agent, or Firm* — Harness, Dickey & Pierce, P.L.C.

(57) ABSTRACT

Disclosed are a system and a method for evaluating exercise. The exercise evaluation system includes a program storage unit storing a plurality of recommendatory exercise programs, a measuring unit measuring exercise intensity of a user, an analyzing unit analyzing a degree of accomplishing the content of a recommendatory exercise program selected by the user from the recommendatory exercise programs by using the measured exercise intensity, and an output unit outputting a result of analysis of the analyzing unit to the user.

4 Claims, 2 Drawing Sheets

(56) References Cited

FOREIGN PATENT DOCUMENTS

Figure 1:
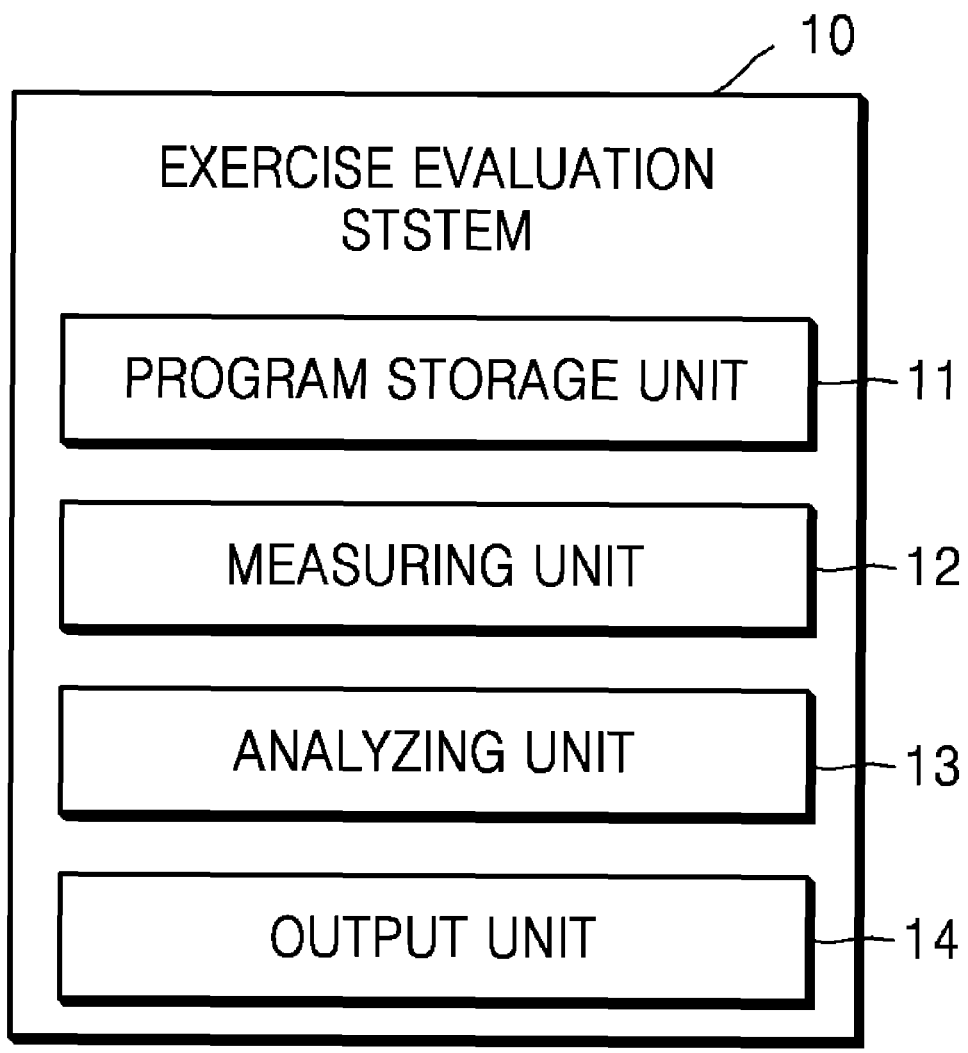

| KR | 10-2009-0089735 | 8/2009 | ............. G06Q 50/00 |
| KR | 10-2011-0043826 | 4/2011 | ............... H04B 1/40 |

* cited by examiner

EXERCISE EVALUATION SYSTEM AND METHOD

CROSS-REFERENCE TO RELATED APPLICATIONS

This application is a national phase application of PCT Application No. PCT/KR2013/008353, filed on 16 Sep. 2013, which claims benefit of Korean Patent Application 10-2012-0145298, filed on 13 Dec. 2012. The entire disclosure of the application identified in this paragraph is incorporated herein by reference.

FIELD

The present invention relates to a system and a method for evaluating exercise, and more particularly, to a system and a method for evaluating exercise in which a degree of accomplishing the content of a recommendatory exercise program selected by a user is automatically analyzed and evaluated using exercise intensity measured as a result of exercise of the user.

BACKGROUND

Since the number of obese and overweight people increases due to hypernutrition and lack of exercise, the need of health care of modern people increasingly grows. In addition, recently, interest in health of ordinary healthy people greatly rises. Due to the possibility of providing ubiquitous health care, development of technology and social need give shape to such interest of people.

To provide this, various exercise programs have been provided. In such exercise programs, for example, it is determined using an amount of exercise, calorie consumption, a heart rate, and a respiration volume whether a user accomplishes a corresponding exercise program. Accordingly, since it is necessary to analyze and determine whether the corresponding exercise program is accomplished using input information of each of exercise programs, it is necessary to separately provide analyzing apparatuses which analyze and determine whether respective exercise programs are accomplished. Due to this, as the variety of exercise programs increases, the number of analyzing apparatuses for determining whether respective exercise programs are accomplished increases. Costs increase to provide analyzing apparatuses.

As a cited reference, there is Korean Patent Publication No. 10-2009-0002175 (published on Jan. 9, 2009).

SUMMARY

An aspect of the present invention is directed to provide a system and a method for evaluating exercise in which a degree of accomplishing the content of a recommendatory exercise program selected by a user is automatically analyzed and provided to the user without additional apparatus regardless of various levels of exercise intensity measured as a result of exercise of the user.

Aspects of the present invention are not limited thereto and additional aspects of the invention will be obvious to one of ordinary skill in the art from the following description.

According to an aspect of the present invention, there is provided an exercise evaluation system including a program storage unit storing a plurality of recommendatory exercise programs, a measuring unit measuring exercise intensity of a user, an analyzing unit analyzing a degree of accomplishing the content of a recommendatory exercise program selected by the user from the recommendatory exercise programs by using the measured exercise intensity, and an output unit outputting a result of analysis of the analyzing unit to the user.

A type of the measured exercise intensity may be one of exercise calorie consumption of the user, exercise oxygen consumption of the user, and an exercise heart rate of the user.

The content of each of the plurality of recommendatory exercise programs may include a recommendatory exercise intensity value to be accomplished by the user, a type of the recommendatory exercise intensity value to be accomplished by the user, a recommendatory exercise time per session in which the user has to continue exercise at the recommendatory exercise intensity value, a recommendatory number of sessions in one day in which the user has to do exercise for the recommendatory exercise time at the recommendatory exercise intensity value in a day, and a recommendatory number of days of doing exercise to keep the recommendatory number of sessions in one day for a certain period.

The content of each of the plurality of recommendatory exercise programs may further include at least one of a title of a corresponding recommendatory exercise program and exercise continuation information which designates whether the user has to continue or discontinue doing exercise at the recommendatory exercise intensity value to satisfy the recommendatory exercise time per session.

The analyzing unit may analyze the degree of accomplishing the content of the selected recommendatory exercise program by using at least one of a ratio of the measured exercise intensity value to the recommendatory exercise intensity value of the content of the selected recommendatory exercise program, a ratio of time in which the measured exercise intensity value within a range of the recommendatory exercise intensity value is continued to the recommendatory exercise time per session of the content of the selected recommendatory exercise program, and a ratio of the number of days of doing exercise keeping the recommendatory number of sessions to the recommendatory number of days of doing exercise of the content of the selected recommendatory exercise program.

The analyzing unit may convert a type of the measured exercise intensity into a type of the exercise intensity value of the recommendatory exercise program selected by the user when the type of the measured exercise intensity differs from the type of the exercise intensity value of the content of the recommendatory exercise program selected by the user.

According to another aspect of the present invention, there is provided an exercise evaluation method including selecting, by a user, a recommendatory exercise program from a plurality of recommendatory exercise programs, measuring exercise intensity of the user, analyzing a degree of accomplishing the content of the selected recommendatory exercise program by using the measured exercise intensity, and outputting a result of the analyzing to the user.

A type of the measured exercise intensity may be one of exercise calorie consumption of the user, exercise oxygen consumption of the user, and an exercise heart rate of the user.

The content of each of the plurality of recommendatory exercise programs may include a recommendatory exercise intensity value to be accomplished by the user, a type of the recommendatory exercise intensity value to be accomplished by the user, a recommendatory exercise time per session in which the user has to continue exercise at the recommendatory exercise intensity value, a recommendatory number of sessions in one day in which the user has to do exercise for the recommendatory exercise time at the recommendatory exercise intensity value in a day, and a recommendatory number of days of doing exercise to keep the recommendatory number of sessions in one day for a certain period.

The content of each of the plurality of recommendatory exercise programs may further include at least one of a title of a corresponding recommendatory exercise program and exercise continuation information which designates whether the user has to continue or discontinue doing exercise at the recommendatory exercise intensity value to satisfy the recommendatory exercise time per session.

The analyzing of the degree of accomplishing the content of the selected recommendatory exercise program may include analyzing the degree of accomplishing the content of the selected recommendatory exercise program by using at least one of a ratio of the measured exercise intensity value to the recommendatory exercise intensity value of the content of the selected recommendatory exercise program, a ratio of time in which the measured exercise intensity value within a range of the recommendatory exercise intensity value is continued to the recommendatory exercise time per session of the content of the selected recommendatory exercise program, and a ratio of the number of days of doing exercise keeping the recommendatory number of sessions to the recommendatory number of days of doing exercise of the content of the selected recommendatory exercise program.

The analyzing of the degree of accomplishing the content of the selected recommendatory exercise program may include converting a type of the measured exercise intensity into a type of the exercise intensity value of the recommendatory exercise program selected by the user when the type of the measured exercise intensity differs from the type of the exercise intensity value of the content of the recommendatory exercise program selected by the user.

Advantageous Effects

According to a system and a method for evaluating exercise in accordance with one embodiment of the present invention, a degree of accomplishing the content of a recommendatory exercise program selected by a user may be automatically analyzed and provided to the user without additional apparatus regardless of various levels of exercise intensity measured as a result of exercise of the user.

DRAWINGS

Figure 2:
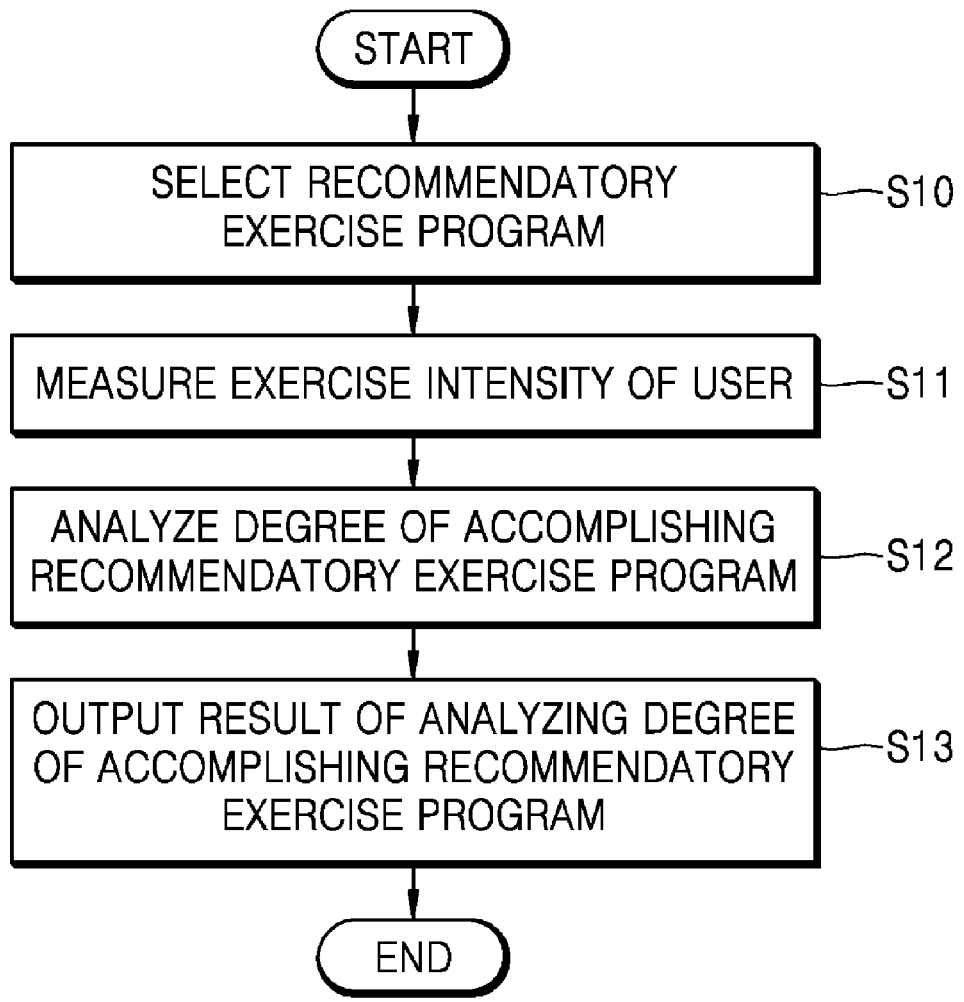

The above objects and other advantages of the present invention will become more apparent by describing in detail preferred embodiments thereof with reference to the attached drawings in which:

FIG. 1 is a configuration diagram of an exercise evaluation system according to an embodiment of the present invention; and FIG. 2 is a flowchart illustrating an exercise evaluation method according to an embodiment of the present invention.

DETAILED DESCRIPTION

Hereinafter, an exemplary embodiment of the present invention will be described in detail with reference to the attached drawings.

The embodiments of the present invention are provided to more perfectly explain the present invention to one of ordinary skill in the art. The following embodiments may be changed into various other forms, and the scope of the present invention is not limited thereto. The embodiments are provided to allow the present disclosure to be more perfect and to fully transfer the inventive concept to one of ordinary skill in the art.

The terms are used herein to describe particular embodiments but will not limit the present invention. As used herein, singular expressions, unless defined otherwise in contexts, include plural expressions. It will be further understood that the terms "comprises" and/or "comprising" used herein specify the presence of stated shapes, numbers, operations, elements, and/or groups thereof, but do not preclude the presence or addition of one or more other shapes, numbers, operations, elements, and/or groups thereof. As used herein, the term "and/or" includes any and all combinations of one or more of the associated listed items.

It will be understood that although the terms "first," "second," etc. may be used herein to describe various components, these components should not be limited by these terms. The terms do not mean a particular order, top and bottom, or merits and demerits but are only used to distinguish one component from another. Accordingly, a first element, area, or portion which will be described below may indicate a second element, area, or portion without deviating from teachings of the present invention.

Hereinafter, the embodiments of the present invention will be described with reference to schematic drawings thereof. Throughout the drawings, for example, according to manufacturing technologies and/or tolerances, illustrated shapes may be modified. Accordingly, the embodiments of the present invention will not be understood to be being limited to certain shapes of illustrated areas but will include changes in shape occurring while being manufactured.

FIG. 1 is a configuration diagram of an exercise evaluation system 10 according to an embodiment of the present invention. Referring to FIG. 1, the exercise evaluation system 10 includes a program storage unit 11, a measuring unit 12, an analyzing unit 13, and an output unit 14.

The program storage unit 11 stores a plurality of recommendatory exercise programs. Here, the content of each of the plurality of recommendatory exercise programs may include a recommendatory exercise intensity value to be accomplished by a user, a type of the recommendatory exercise intensity value to be accomplished by the user, a recommendatory exercise time per session (corresponding to several minutes per session) in which the user has to continue exercise at the recommendatory exercise intensity value, a recommendatory number of sessions in one day (corresponding to several sessions per day) in which the user has to do exercise for the recommendatory exercise time at the recommendatory exercise intensity value in a day, and a recommendatory number of days of doing exercise to keep the recommendatory number of sessions in one day for a certain period (corresponding to several days per week). In addition, the content of each of the plurality of recommendatory exercise programs may further include at least one of a title of a corresponding recommendatory exercise program and exercise continuation information which designates whether the user has to continue or discontinue doing exercise at the recommendatory exercise intensity value to satisfy the recommendatory exercise time per session.

For example, the program storage unit 11 may store recommendatory exercise programs for hypertensive patients and recommendatory exercise programs for obese people. Here, in the content of the recommendatory exercise program for hypertensive patients, the type of the recommendatory exercise intensity value may be "exercise oxygen consumption VO2R" in this case, the recommendatory exercise intensity value, that is, recommendatory exercise oxygen consumption may be "40%", the recommendatory exercise time per session to continue doing exercise with the recommendatory oxygen consumption may be "30 minutes", the recommendatory number of sessions per day to do exercise for the recommendatory exercise time of 30 minutes at the recommendatory exercise intensity value of 40% may be "three times per day", the recommendatory number of days per certain period of doing exercise three times which is the recommendatory number of sessions may be "seven days per week", and the exercise continuation information may be "continue." However, this is merely an example and is not limited thereto.

In the content of the recommendatory exercise program for obese people, the type of the recommendatory exercise intensity value may be "Calories (Kcal)". In this case, the recommendatory exercise intensity value, that is, a recommendatory exercise calories may be "2000 Kcal", the recommendatory exercise time per session to continue doing exercise to consume the recommendatory exercise calories may be "2 to 3 hours", the recommendatory number of days of doing exercise keeping the recommendatory number of sessions may be "six days per week", and the exercise continuation information may be "irrelevant". However, this is merely an example and is not limited thereto.

The measuring unit 12 measures the exercise intensity of the user. The measuring unit 12 may be included inside the exercise evaluation system 10 or may be provided outside the exercise evaluation system 10 as an additional apparatus. Here, the type of exercise intensity measured using the measuring unit 12 may include an amount of exercise of the user, exercise calorie consumption of the user, exercise oxygen consumption of the user, and an exercise heart rate of the user. Accordingly, the measuring unit 12 may be one of an exercise amount measuring device, a pedometer, a cardiotachometer, and an aeroplethysmograph.

The exercise calorie consumption may have a unit of Kcal or metabolic equivalent (MET). The exercise oxygen consumption of the user may be designated as a symbol of VO2R and designates oxygen consumption obtained by subtracting oxygen consumption necessary for basal metabolism from oxygen consumption VO2Max which people maximally respire. That is, the exercise calorie consumption of the user indicates oxygen consumption of the user used during exercise. Throughout the specification, a unit of oxygen consumption is liter per minute (l/m). The exercise heart rate of the user may be heart rate reserve (HRR). HRR is a heart rate of a human being available for exercise. That is, HRR designates a difference between resting heart rate $HR_{rest}$ and max heart rate $HR_{Max}$.

The analyzing unit 12 analyzes a degree of accomplishing the content of a recommendatory exercise program selected by the user from the recommendatory exercise programs using the measured exercise intensity. Here, the analyzing unit 12 may analyze the degree of the content of the selected recommendatory exercise program by using at least one of a ratio of the measured exercise intensity value to a recommendatory exercise intensity value of the content of the selected recommendatory exercise program, a ratio of time in which the measured exercise intensity value within a range of the recommendatory exercise intensity value is continued to the recommendatory exercise time per session of the content of the selected recommendatory exercise program, and a ratio of the number of days of doing exercise keeping the recommendatory number of sessions to the recommendatory number of days of doing exercise of the content of the selected recommendatory exercise program.

As an example, when the selected recommendatory exercise program is "a recommendatory exercise program for hypertensive patients", a recommendatory exercise intensity value is "40%", a recommendatory exercise time per session of continuing exercise at the recommendatory exercise intensity value is "30 minutes", and a recommendatory number of days of doing exercise while keeping a recommendatory number of sessions which the hypertensive patients have to do exercise for the recommendatory exercise time at the recommendatory exercise intensity for a certain period is seven days per week, the measured exercise intensity value is 30%, a time of continuing a measured exercise intensity value within the range of the recommendatory exercise intensity value is 20 minutes, and the number of days of keeping the recommendatory number of sessions is five days. Here, a degree of a user to accomplish "the recommendatory exercise program for hypertensive patients" may be obtained using at least one of a ratio of the measured exercise intensity value of 30% to the recommendatory exercise intensity value of 40%, a ratio of the measured time of continuing the measured exercise intensity value within the recommendatory exercise intensity value, which is 20 minutes, to the recommendatory exercise time per session, which is 30 minutes, and a ratio of the number of days of doing exercise while keeping the recommendatory number of sessions, which is five days, to the recommendatory number of days of doing exercise, which is seven days. Here, when the degree of accomplishing "the recommendatory exercise program for hypertensive patients" is obtained as a ratio of the measured exercise intensity value of 30% to the recommendatory exercise intensity value of 40%, the degree of accomplishing "the recommendatory exercise program for hypertensive patients" may be 75%. However, this is merely an example and is not limited thereto.

Meanwhile, when a type of the measured exercise intensity differs from a type of an exercise intensity value of the content of the recommendatory exercise program selected by the user, the analyzing unit 13 may convert the type of the measured exercise intensity into the type of the exercise intensity value of the content of the recommendatory exercise program selected by the user. As an example, the analyzing unit 13 may convert VO2R into MET. An equation for the converting this may be "MET=(((MET_VO2MAX−1)/100)*VO2R)+1". As another example, the analyzing unit 13 may convert VO2MAX into MET. An equation for the converting this may be "MET=MET_VO2MAX/100)*VO2MAX". MET_VO2MAX is a value obtained by converting VO2MAX into an MET unit.

The output unit 14 outputs a result of analysis of the analyzing unit 13 to the user. As an example, the output unit 14 may visually or audibly output the result of analysis of the analyzing unit 13 to the user. As another example, the output unit 14 may include a communication module able to access the Internet and a network to perform communication and may transmit the result of analysis of the analyzing unit 13 to a user terminal at a distant place.

The configuration of the exercise evaluation system shown in FIG. 1 is simply classified from functional perspectives and does not mean a real application method or a hardware system. One or more modules shown in FIG. 1 may be integrated or segmented, which is obvious to one of ordinary skill in the art.

FIG. 2 is a flowchart illustrating an exercise evaluation method according to an embodiment of the present invention. Referring to FIG. 2, the exercise evaluation method may be performed by the exercise evaluation system shown in FIG. 1.

A recommendatory exercise program is selected by a user from a plurality of recommendatory exercise programs (S10). Here, the content of each of the plurality of recommendatory exercise programs may include a recommendatory exercise intensity value to be accomplished by the user, a type of the recommendatory exercise intensity value to be accomplished by the user, a recommendatory exercise time per session (corresponding to several minutes per session) in which the user has to continue exercise at the recommendatory exercise intensity value, a recommendatory number of sessions in one day (corresponding to several sessions per day) in which the user has to do exercise for the recommendatory exercise time at the recommendatory exercise intensity value in a day, and a recommendatory number of days of doing exercise to accomplish the recommendatory number of sessions in one day for a certain period (corresponding to several days per week). In addition, the content of each of the plurality of recommendatory exercise programs may further include at least one of a title of a corresponding recommendatory exercise program and exercise continuation information which designates whether the user has to continue or discontinue doing exercise at the recommendatory exercise intensity value to satisfy the recommendatory exercise time per session.

Exercise intensity of the user is measured (S11). Here, a type of the measured exercise intensity may be one of an amount of exercise of the user, exercise calorie consumption of the user, exercise oxygen consumption of the user, and an exercise heart rate of the user.

A degree of the content of the recommendatory exercise program selected by the user is analyzed using the measured exercise intensity (S12). As an example, the degree of the content of the selected recommendatory exercise program may be analyzed by using at least one of a ratio of the measured exercise intensity value to a recommendatory exercise intensity value of the content of the selected recommendatory exercise program, a ratio of time in which the measured exercise intensity value within a range of the recommendatory exercise intensity value is continued to the recommendatory exercise time per session of the content of the selected recommendatory exercise program, and a ratio of the number of days of doing exercise while keeping the recommendatory number of sessions to the recommendatory number of days of doing exercise of the content of the selected recommendatory exercise program. However, it is not limited thereto.

Here, a type of the measured exercise intensity may differ from a type of exercise intensity in the selected recommendatory exercise program. Accordingly, it is necessary to convert the type of the measured exercise intensity into the type of the exercise intensity of the recommendatory exercise program selected by the user. As an example, when the type of the measured exercise intensity is VO2R and the type of the exercise intensity of the selected recommendatory exercise program is MET, it is necessary to convert VO2R into MET. This is merely an example and is not limited thereto. The result of analysis is output to the user (S13). As an example, the result of analysis may be visually or audibly output to the user. Furthermore, the result of analysis may be transmitted to the user terminal located in a distant place through a communication module accessible to a network.

As described above, exemplary embodiments of the present invention have been described. While the present invention has been particularly shown and described with reference to exemplary embodiments thereof, it will be understood by those of ordinary skill in the art that various changes in form and details may be made therein without departing from the spirit and scope of the present invention as defined by the following claims. Therefore the embodiments described above would be considered in a descriptive way, not in a limitative way. Accordingly, the scope of the present invention is not limited to the embodiments described above and it would be understood to include the content disclosed in the claims and equivalents thereof.

INDUSTRIAL APPLICABILITY

The present invention may be applied to an exercise-medical field.

What is claimed is:
1. An exercise evaluation system comprising:
a memory storing a plurality of recommendatory exercise programs, each recommendatory exercise program specifying a type and value of exercise intensity to be maintained for a specified time per session, number of sessions per day, and number of days, the exercise intensity including at least one of an exercise calorie consumption of a user, an exercise oxygen consumption of the user, and an exercise heart rate of the user;
a measuring unit measuring exercise intensity of the user via one of a pedometer, a cardiotachometer and an aeroplethysmograph; and
a processor communicatively coupled to the memory and the measuring unit to:
analyze a degree of accomplishing the content of a recommendatory exercise program selected by the user from the recommendatory exercise programs by using at least one of a ratio of a measured exercise intensity value to the recommendatory exercise intensity value of the content of the selected recommendatory exercise program, a ratio of a time in which the measured exercise intensity value is continued within a range of the recommendatory exercise intensity value to the recommendatory exercise time per session of the content of the selected recommendatory exercise program, and a ratio of a number of days of exercising the recommendatory number of sessions to the recommendatory number of days of doing exercise of the content of the selected recommendatory exercise program;
convert a type of the measured exercise intensity into a type of the exercise intensity value of the recommendatory exercise program selected by the user when the type of the measured exercise intensity differs from the type of the exercise intensity value of the content of the recommendatory exercise program selected by the user; and
output a result of the analysis to the user.
2. The exercise evaluation system of claim 1, wherein the content of each of the plurality of recommendatory exercise programs further comprises at least one of a title of a corresponding recommendatory exercise program and exercise continuation information which designates whether the user has to continue or discontinue doing exercise at the recommendatory exercise intensity value to satisfy the recommendatory exercise time per session.

3. An exercise evaluation method comprising:

selecting, by a user, a recommendatory exercise program from a plurality of recommendatory exercise programs, each recommendatory exercise program specifying a type and value of exercise intensity to be maintained for a specified time per session, number of sessions per day, and number of days, the exercise intensity including at least one of an exercise calorie consumption of a user, an exercise oxygen consumption of the user, and an exercise heart rate of the user;

measuring exercise intensity of the user via one of a pedometer, a cardiotachometer and an aeroplethysmograph;

analyzing a degree of accomplishing the content of the selected recommendatory exercise program by using at least one of a ratio of a measured exercise intensity value to the recommendatory exercise intensity value of the content of the selected recommendatory exercise program, a ratio of a time in which the measured exercise intensity value is continued within a range of the recommendatory exercise intensity value to the recommendatory exercise time per session of the content of the selected recommendatory exercise program, and a ratio of a number of days of exercising the recommendatory number of sessions to the recommendatory number of days of doing exercise of the content of the selected recommendatory exercise program;

converting a type of the measured exercise intensity into a type of the exercise intensity value of the recommendatory exercise program selected by the user when the type of the measured exercise intensity differs from the type of the exercise intensity value of the content of the recommendatory exercise program selected by the user; and outputting a result of the analyzing to the user.

4. The exercise evaluation method of claim 3, wherein the content of each of the plurality of recommendatory exercise programs further comprises at least one of a title of a corresponding recommendatory exercise program and exercise continuation information which designates whether the user has to continue or discontinue doing exercise at the recommendatory exercise intensity value to satisfy the recommendatory exercise time per session.

* * * * *